(12) United States Patent
Rubio

(10) Patent No.: US 6,475,203 B1
(45) Date of Patent: Nov. 5, 2002

(54) FEMININE HYGIENE PAD

(76) Inventor: Ilse Rubio, 1402 N. Alta Vista Blvd. #208, Los Angeles, CA (US) 90046

( * ) Notice: Subject to any disclaimer, the term of this patent is extended or adjusted under 35 U.S.C. 154(b) by 0 days.

(21) Appl. No.: 09/558,354

(22) Filed: Apr. 26, 2000

Related U.S. Application Data

(63) Continuation of application No. 29/089,449, filed on Jun. 15, 1998, now Pat. No. Des. 426,887.

(51) Int. Cl.[7] ............................................. A61F 13/15
(52) U.S. Cl. .............................. 604/385.03; 604/387
(58) Field of Search ........................ 604/386, 387, 604/354, 385.03, 385.14

(56) References Cited

U.S. PATENT DOCUMENTS

| | | | | |
|---|---|---|---|---|
| 3,983,873 A | * | 10/1976 | Hirschman | 128/285 |
| 4,678,464 A | * | 7/1987 | Holtman | 604/385 R |
| 4,781,713 A | * | 11/1988 | Welch et al. | 604/385.1 |
| RE33,351 E | * | 9/1990 | Papajohn | 604/387 |
| 5,037,417 A | * | 8/1991 | Ternstrom et al. | 604/385.2 |
| 5,127,911 A | * | 7/1992 | Baharav | 604/385.1 |
| 5,241,710 A | * | 9/1993 | Lockhart | 2/406 |
| 5,350,067 A | * | 9/1994 | Beltran | 206/440 |
| 5,358,500 A | * | 10/1994 | Lavon et al. | 604/385.2 |
| 5,383,868 A | * | 1/1995 | Hyun | 604/385.1 |
| 5,383,871 A | * | 1/1995 | Carlin et al. | 604/385.2 |
| 5,484,429 A | * | 1/1996 | Vukos et al. | 604/385.1 |
| 5,520,675 A | * | 5/1996 | Knox-Sigh | 604/385.1 |
| 5,683,373 A | * | 11/1997 | Darby | 604/385.1 |
| 5,690,625 A | * | 11/1997 | Widlund | 604/385.1 |
| 5,713,886 A | * | 2/1998 | Sturino | 604/390 |
| D394,503 S | * | 5/1998 | Perrini | D24/125 |
| 5,792,129 A | * | 8/1998 | Johansson et al. | 604/387 |
| 5,827,261 A | * | 10/1998 | Osborn, III et al. | 604/387 |
| D411,006 S | * | 6/1999 | Nixon et al. | D24/125 |
| D416,324 S | * | 11/1999 | Nixon et al. | D24/125 |
| D424,195 S | * | 5/2000 | Talon | D24/125 |
| D426,887 S | * | 6/2000 | Rubio | D24/125 |
| D439,331 S | * | 3/2001 | Mitchell | D24/125 |
| D444,230 S | * | 6/2001 | Renz et al. | D24/125 |
| D445,498 S | * | 7/2001 | Renz et al. | D24/125 |

FOREIGN PATENT DOCUMENTS

WO    WO 90/04956    *   5/1990    ............ A61F/13/16

* cited by examiner

*Primary Examiner*—Aaron J. Lewis
*Assistant Examiner*—Michael Bogart

(57) ABSTRACT

A feminine hygiene pad having a wide absorbent front portion and a narrower, elongated rear portion of sufficient length to be retained between the buttocks of a user to better fit against the user's body and thereby control rearward leakage of fluid. The hygienic pad is smaller and better fitting and can be worn more discreetly with small sized and tight fitting garments.

15 Claims, 3 Drawing Sheets

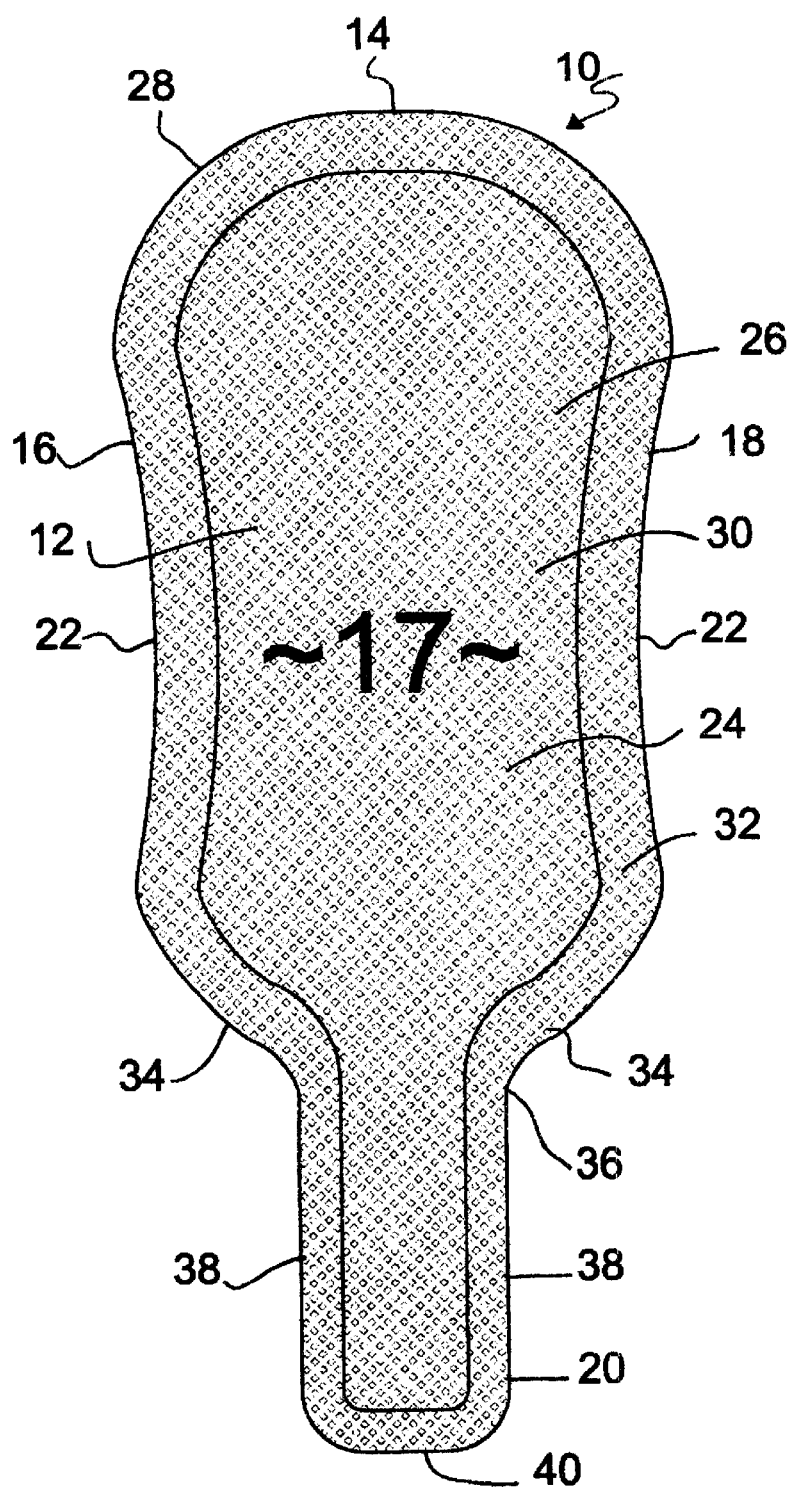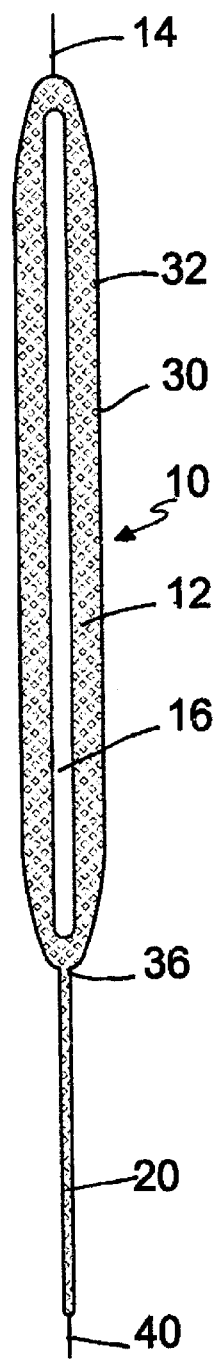
FIG. 5
FIG. 3

FEMININE HYGIENE PAD

CROSS REFERENCE TO RELATED APPLICATIONS

This application is a continuation of the application No. 29/089,449 filed Jun. 15, 1998.

This application claims the benefit of the filing date of Ser. No. 29/089,449, now issued as U.S. Design Pat. No. D426887.

STATEMENT REGARDING FEDERALLY SPONSORED RESEARCH OR DEVELOPMENT

Not Applicable.

REFERENCE TO A MICROFICHE APPENDIX

Not Applicable.

BACK GROUND OF THE INVENTION

It is the object of the present invention to provide and minimize the size of an absorbent pad intended to prevent the rearward leakage of menstrual fluid. It is another object of the present invention to provide a means for a woman to sleep on her back without the risk of posterior leakage. It is another object of the present invention to provide a minimal sized absorbent pad to be worn with small sized textiles or tight fitting garments.

One feature of this aspect of the invention is that the pad incorporates an ELONGATED REARWARD APPENDAGE.

Another feature of this aspect of the invention is that the elongated rearward appendage shall be placed between the buttocks, securing its position to the wearer and preventing any liquid flow.

Prior Feminine Pads have not addressed the need for stoppage of the flow in the rearward or posterior direction, namley to the buttocks and posterior of the upper thighs.The means of stopping the rearward flow and retention of the device in the crotch of the user are both novel and previously undocumented. Prior art pads are oversized.

SUMMARY OF THE INVENTION

Set forth below is a brief summary of the invention which achieves the foregoing and other objectives and provides the foregoing and hereafter stated benefits and advantages in accordance with the structure, function and results of the present invention as embodied and broadly described herein.

This feature is specific to, but not limited by this specificity, the need to prevent leakage of fluids,the main point of absorbency is in the main portion of the pad. Another feature of this aspect of the Feminine Hygiene Pad is that it is of minimal size and is intended to be worn with small sized textile and tight fitting garments.

BRIEF DESCRIPTION OF THE SEVERAL VIEWS OF THE DRAWING

FIG. 6 Is a top edge view there of;

DETAILED DESCRIPTION OF THE INVENTION

Figure 1:
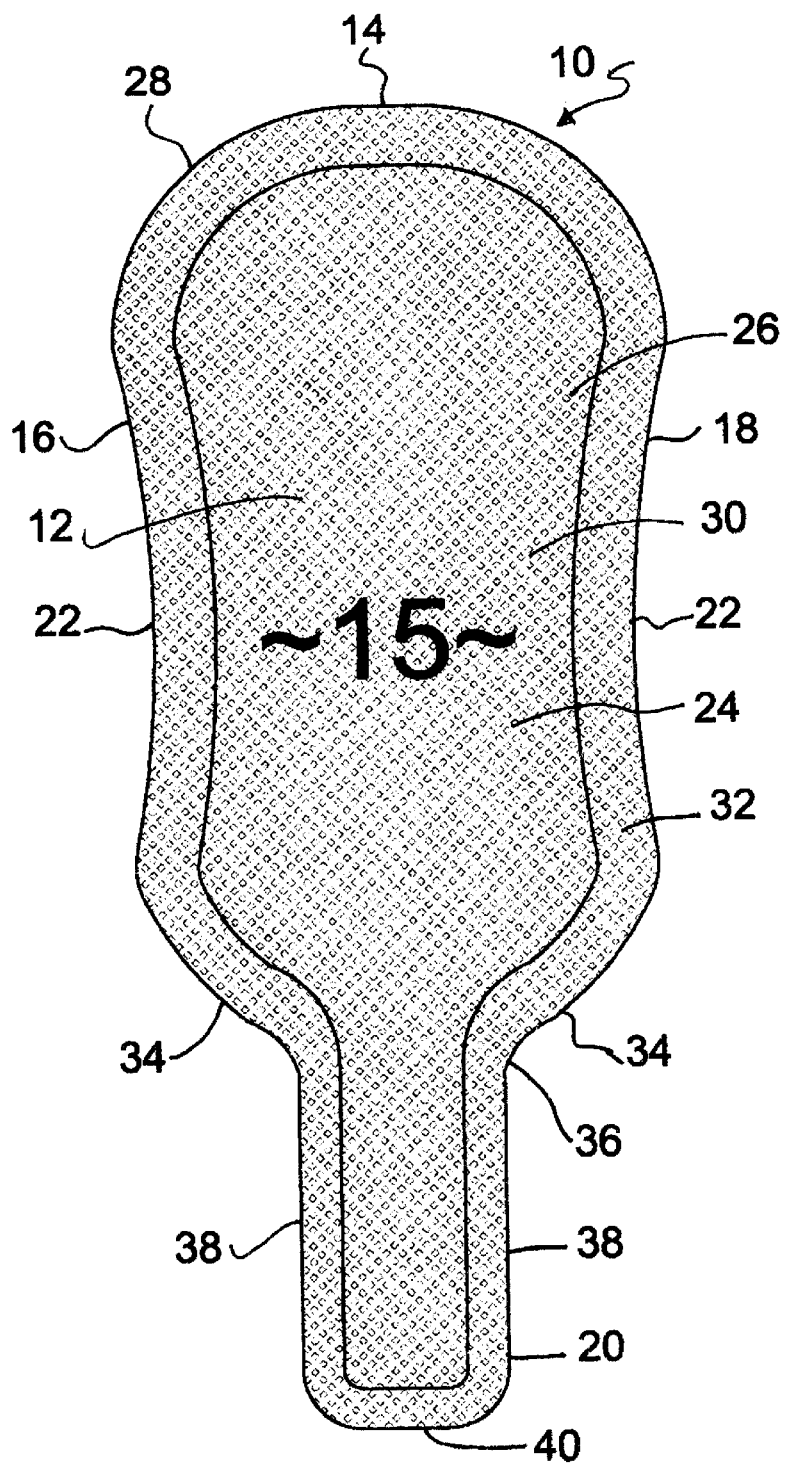
FIG. 1 Is a front elevational view of a Feminine Hygiene Pad

An absorbent article; as apparent in FIGS. 1 through 6, the preferred embodiment consists of an absorbent body (1). The Absorbent body (1) is adhered or otherwise permanently bonded at its perimeter by the bonded edge. (2) A positioning point is formed on the main absorbent portion of the pad and an absorbent point is formed on the main portion of the pad. (3) The Elongated Rearward Appendage is fabricated of the same material as, and at the same time as the Absorbent body. The ELONGATED REARWARD APPENDICE is considered to be integral to the Absorbent Body (1) and the invention as a whole.

I claim:

1. A feminine hygiene pad having a wider absorbent forward pad portion and a relatively narrow rear portion adapted to be worn between the buttocks of a user, said rear portion having a rear edge and a rear width between rear side edges, said forward pad portion having forward side edges including divergent side edge portions diverging from said rear side edges and a transition from said divergent side edge portions to non-divergent side edge portions;

said forward pad portion increasing in width between said divergent side edges to a location along said longitudinal dimension corresponding to a pad width of at least twice said rear width;

said forward pad portion having a forward pad length measured from said location along said longitudinal dimension to a front edge of said pad;

said rear portion having a rear length measured from said rear edge to said location along said longitudinal dimension;

said forward pad length being at least one and one half times longer than said rear length; and a border of relatively thin material along at least some of said side edges, said rear edge and said front edge.

2. The feminine hygiene pad of claim 1 wherein said rear portion is integral with said forward pad portion.

3. The feminine hygiene pad of claim 1 wherein said rear portion is sized and shaped to be retained between the buttocks of a user of said pad.

4. The feminine hygiene pad of claim 1 wherein said absorbent forward pad portion is substantially thicker than a thickness of said rear portion.

5. The feminine hygiene pad of claim 1 wherein said absorbent forward pad portion is much thicker than a thickness of said rear portion.

6. The feminine hygiene pad of claim 1 wherein said forward pad portion has a wider front and a narrower mid-portion, said mid-portion being at least twice as wide as a width of said rear portion.

7. The feminine hygiene pad of claim 1 wherein said rear portion is made of the same material as the forward pad portion.

8. The feminine hygiene pad of claim 1 wherein said forward pad portion has an absorbent body bonded along a perimeter thereof by a bonded edge of said relatively thin material.

9. The feminine hygiene pad of claim 1, said hygiene pad further having a continuous upper surface and a continuous bottom surface, each said surface being common to said forward pad portion and said rear pad portion.

10. The feminine hygiene pad of claim 1 wherein said forward pad length is about twice as long as said rear length.

11. A feminine hygiene pad having a wider absorbent forward pad portion and a relatively narrow rear portion adapted to be worn between the buttocks of a user, said rear portion having a rear edge and a rear width between rear side edges, said forward pad portion having forward side edges including divergent side edge portions diverging from said rear side edges and a transition from said divergent side edge portions to non-divergent side edge portions;

said forward side edges of said forward pad portion having inturned side edge portions defining therebetween a pad mid-portion of minimum width longitudinally located between pad portions of greater width than said minimum width and also longitudinally located between said transition and a front edge of said pad;

said minimum width being greater than said rear width; and a border of relatively thin material along at least some of said side edges, said rear edge and said front edge.

12. The pad of claim 11 wherein said minimum width is more than twice said rear width of said rear portion.

13. The pad of claim 11 wherein said inturned side edges comprise concavely curved portions of said forward side edges.

14. The pad of claim 11 wherein said pad mid-portion of minimum width is located approximately midway between said divergent side edge portions and said front edge of said pad.

15. The pad of claim 11 wherein said forward pad portion increases in width between said divergent side edges to a location along said longitudinal dimension corresponding to a pad width of at least twice said rear width;

said forward pad portion having a forward pad length measured from said location along said longitudinal dimension to a front edge of said pad;

said rear portion having a rear length measured from said rear edge to said location along said longitudinal dimension;

said forward pad length being substantially longer than said rear length.

* * * * *

UNITED STATES PATENT AND TRADEMARK OFFICE
CERTIFICATE OF CORRECTION

PATENT NO.    : 6,475,203 B1
DATED         : November 5, 2002
INVENTOR(S)   : Ilse Rubio It is certified that error appears in the above-identified patent and that said Letters Patent is hereby corrected as shown below:

The title page should be deleted and substitute therefore the attached title page.

Delete drawing sheets 1-6, and substitute therefore the drawing sheets, consisting of FIGS. 1-6 as shown on the attached pages Please replace columns 1-6, with the new specification in columns 1-6 as per the attached pages <u>Title page,</u>
Item [76], the inventor's address should read -- P.O. Box 93064, Los Angeles, CA 90093 USA --

Signed and Sealed this

Twenty-fifth Day of November, 2003

JAMES E. ROGAN
*Director of the United States Patent and Trademark Office*

United States Patent
Rubio

(10) Patent No.: US 6,475,203 B1
(45) Date of Patent: Nov. 5, 2002

(54) FEMININE HYGIENE PAD

(76) Inventor: Ilse Rubio, 1402 N. Alta Vista Blvd. #208, Los Angeles, CA (US) 90046

(*) Notice: Subject to any disclaimer, the term of this patent is extended or adjusted under 35 U.S.C. 154(b) by 0 days.

(21) Appl. No.: 09/558,354

(22) Filed: Apr. 26, 2000

Related U.S. Application Data

(63) Continuation of application No. 29/089,449, filed on Jun. 15, 1998, now Pat. No. Des. 426,887.

(51) Int. Cl.$^7$ .................................................. A61F 13/15
(52) U.S. Cl. ................................... 604/385.03; 604/387
(58) Field of Search ................................. 604/386, 387, 604/354, 385.03, 385.14

(56) References Cited

U.S. PATENT DOCUMENTS

| | | | | |
|---|---|---|---|---|
| 3,983,873 A | * | 10/1976 | Hirschman | 128/285 |
| 4,678,464 A | * | 7/1987 | Holtman | 604/385 R |
| 4,781,713 A | * | 11/1988 | Welch et al. | 604/385.1 |
| RE33,351 E | * | 9/1990 | Papajohn | 604/387 |
| 5,037,417 A | * | 8/1991 | Ternstrom et al. | 604/385.2 |
| 5,127,911 A | * | 7/1992 | Baharav | 604/385.1 |
| 5,241,710 A | * | 9/1993 | Lockhart | 2/406 |
| 5,350,067 A | * | 9/1994 | Beltran | 206/440 |
| 5,358,500 A | * | 10/1994 | Lavon et al. | 604/385.2 |
| 5,383,868 A | * | 1/1995 | Hyun | 604/385.1 |
| 5,383,871 A | * | 1/1995 | Carlin et al. | 604/385.2 |
| 5,484,429 A | * | 1/1996 | Vukos et al. | 604/385.1 |
| 5,520,675 A | * | 5/1996 | Knox-Sigh | 604/385.1 |
| 5,683,373 A | * | 11/1997 | Darby | 604/385.1 |
| 5,690,625 A | * | 11/1997 | Widlund | 604/385.1 |
| 5,713,886 A | * | 2/1998 | Sturino | 604/390 |
| D394,503 S | * | 5/1998 | Perrini | D24/125 |
| 5,792,129 A | * | 8/1998 | Johansson et al. | 604/387 |
| 5,827,261 A | * | 10/1998 | Osborn, III et al. | 604/387 |
| D411,006 S | * | 6/1999 | Nixon et al. | D24/125 |
| D416,324 S | * | 11/1999 | Nixon et al. | D24/125 |
| D424,195 S | * | 5/2000 | Talon | D24/125 |
| D426,887 S | * | 6/2000 | Rubio | D24/125 |
| D439,331 S | * | 3/2001 | Mitchell | D24/125 |
| D444,230 S | * | 6/2001 | Renz et al. | D24/125 |
| D445,498 S | * | 7/2001 | Renz et al. | D24/125 |

FOREIGN PATENT DOCUMENTS

| | | | | |
|---|---|---|---|---|
| WO | WO 90/04956 | * | 5/1990 | A61F/13/16 |

* cited by examiner

*Primary Examiner*—Aaron J. Lewis
*Assistant Examiner*—Michael Bogart

(57) ABSTRACT

A feminine hygiene pad having a wide absorbent front portion and a narrower, elongated rear portion of sufficient length to be retained between the buttocks of a user to better fit against the user's body and thereby control rearward leakage of fluid. The hygienic pad is smaller and better fitting and can be worn more discreetly with small sized and tight fitting garments.

15 Claims, 3 Drawing Sheets

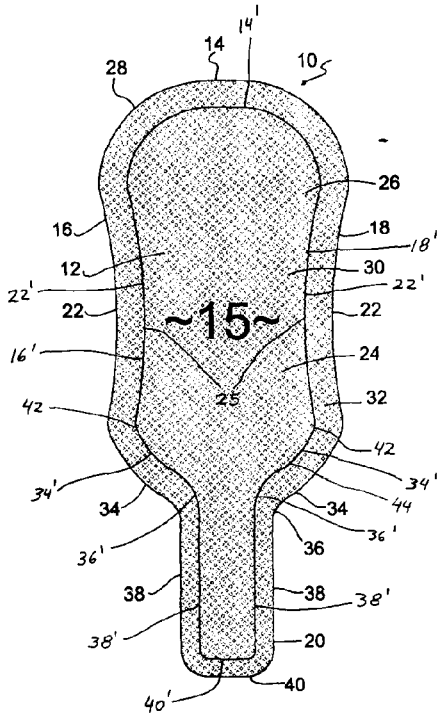

FEMININE HYGIENE PAD

This application is a continuation and claims the benefit of the filing date of Ser. No. 29/089,449, now issued as U.S. Des. Pat. No. D426887.

BACKGROUND OF THE INVENTION

1. Field of the Invention

This invention relates to feminine hygiene pads.

2. State of the Prior Art

Feminine hygiene pads are disposable, liquid absorbent pads applied to the crotch area by women in order to absorb menstrual fluids. Existing feminine hygiene pads are symmetrical in shape along a longitudinal dimension, with wider rounded ends and a narrower mid-portion defined between opposite concave side edges. In existing pads the wide rear portion of the pad fits over the buttocks and allows menstrual fluids to leak to the rear of the thighs and onto the buttocks. This prevents women wearing these pads from sleeping on their backs in order to control such leakage. Another shortcoming of existing pads is that they are oversized and cannot be worn discreetly with skimpy or small garments or tight fitting clothing.

A need exists for improved feminine hygiene pads which fit better to the contour of the user's body to control rearward leakage of menstrual fluid and to permit discreet use of the pad with close fitting or skimpy clothing.

SUMMARY OF THE INVENTION

This invention addresses the aforementioned need by providing a feminine hygiene pad having an absorbent forward pad portion, the forward portion having a longitudinal dimension and a transverse dimension, and a rear portion extending from the forward portion along the longitudinal dimension and having a width lesser than one half of the transverse dimension.

The width of the rear portion may be about one-third of the transverse dimension and the rear portion may have a length of approximately one-third of the aforementioned longitudinal dimension. The forward portion may have a wider front and a narrower mid-portion, both the forward portion and the mid-portion being substantially wider than the rear portion. The rear portion is of sufficient length in the direction of the longitudinal dimension to be retained between the buttocks of a user, and preferably the rear portion is formed integrally with the forward portion and is made of the same material as the forward portion. The forward portion has an absorbent body bonded along a perimeter thereof by a bonded edge. The mid-portion has two opposite concavely curved sides and a convexly curved front edge, while the rear portion may have generally parallel sides in the direction of the longitudinal dimension, such that the rear portion is a generally rectangular elongated tab.

More generally, this invention is a feminine hygiene pad having a longitudinal dimension along the length thereof, a relatively wide absorbent frontal portion and a much narrower elongated rear portion sized for retention between the buttocks of a user.

Set forth below is a brief summary of the invention which achieves the foregoing and other objectives and provides the foregoing and hereafter stated benefits and advantages in accordance with the structure, function and results of the present invention as embodied and broadly described herein. This feature is specific to, but not limited by this specificity, the need to prevent leakage of fluids, the main point of absorbency is in the main portion of the pad. Another feature of this aspect of the Feminine Hygiene Pad is that it is of minimal size and is intended to be worn with small sized textile and tight fitting garments.

BRIEF DESCRIPTION OF THE DRAWINGS

Figure 2:
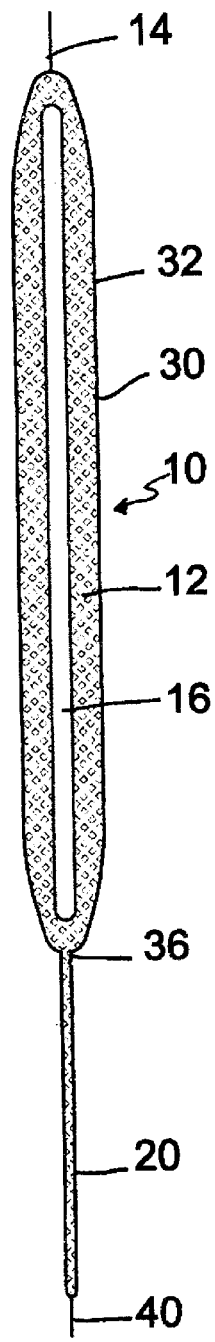
FIG. 2 Is a right side edge elevational view thereof.
Figure 4:
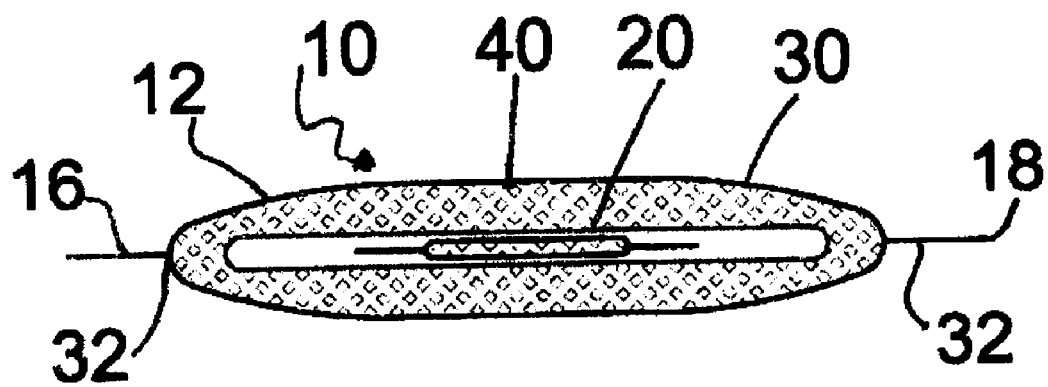
FIG. 4 Is a bottom edge view thereof.
Figure 6:
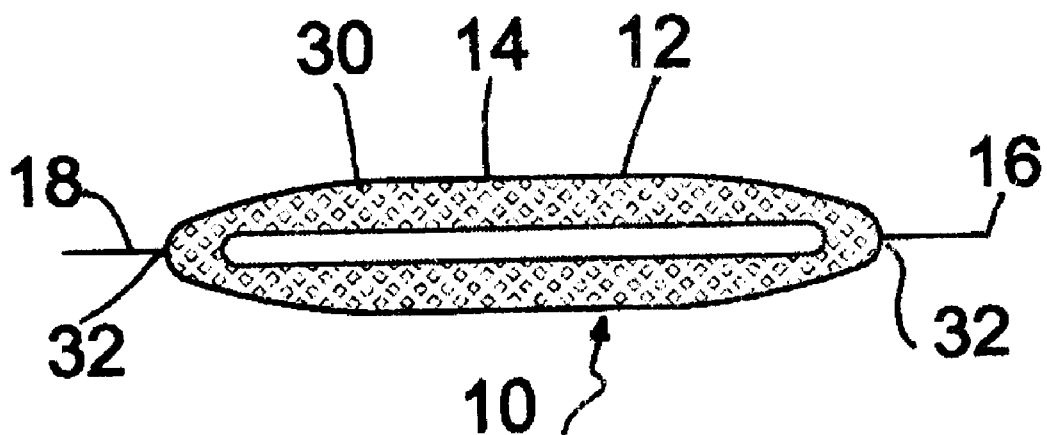
Figure 1:
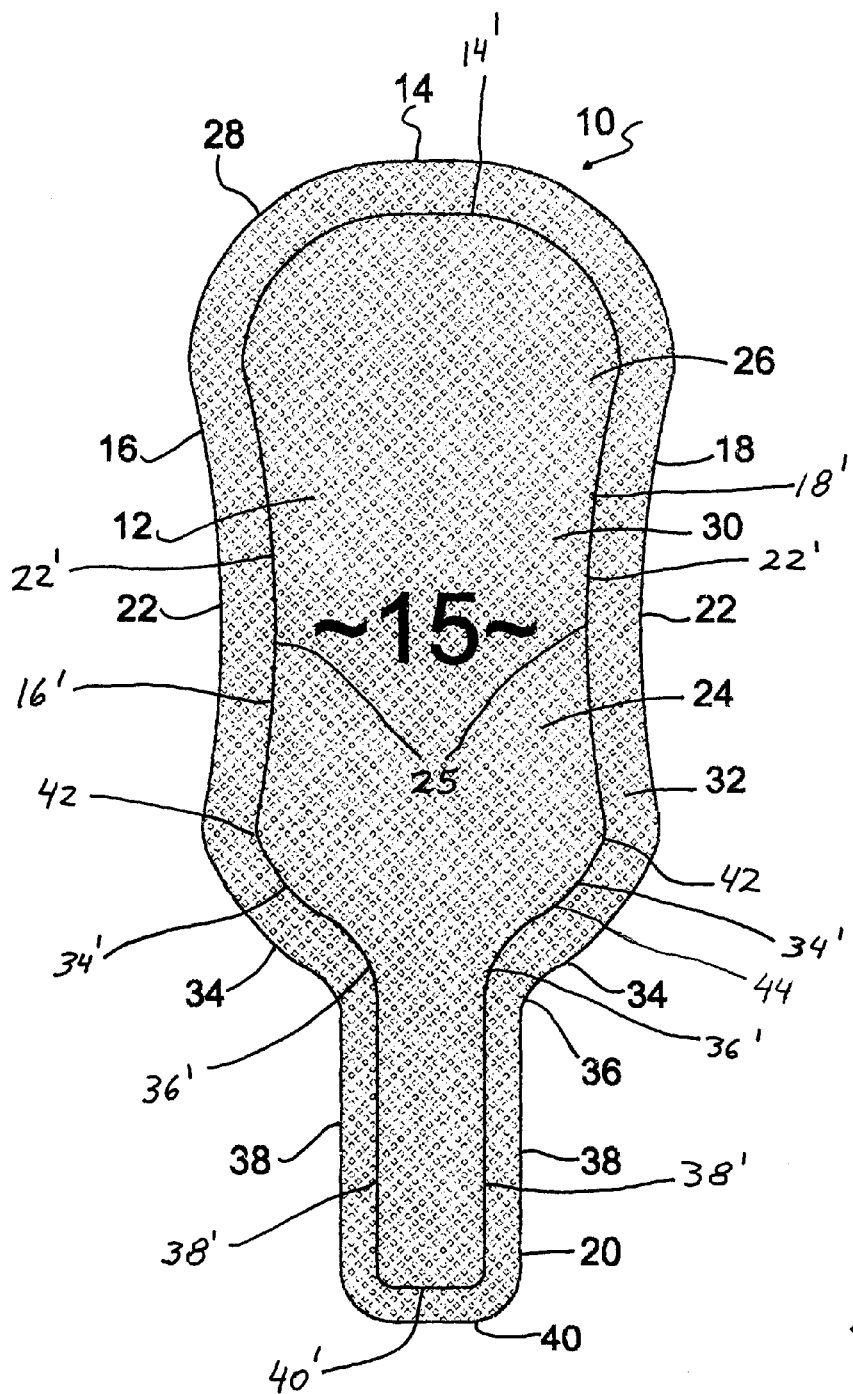
Figure 2:
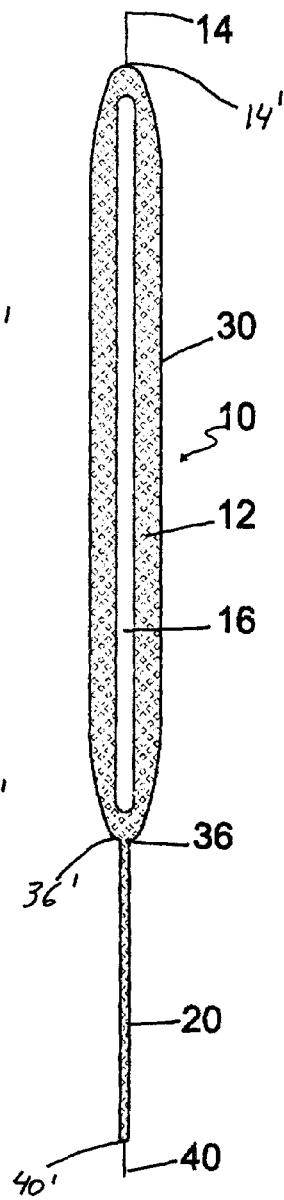
Figure 5:
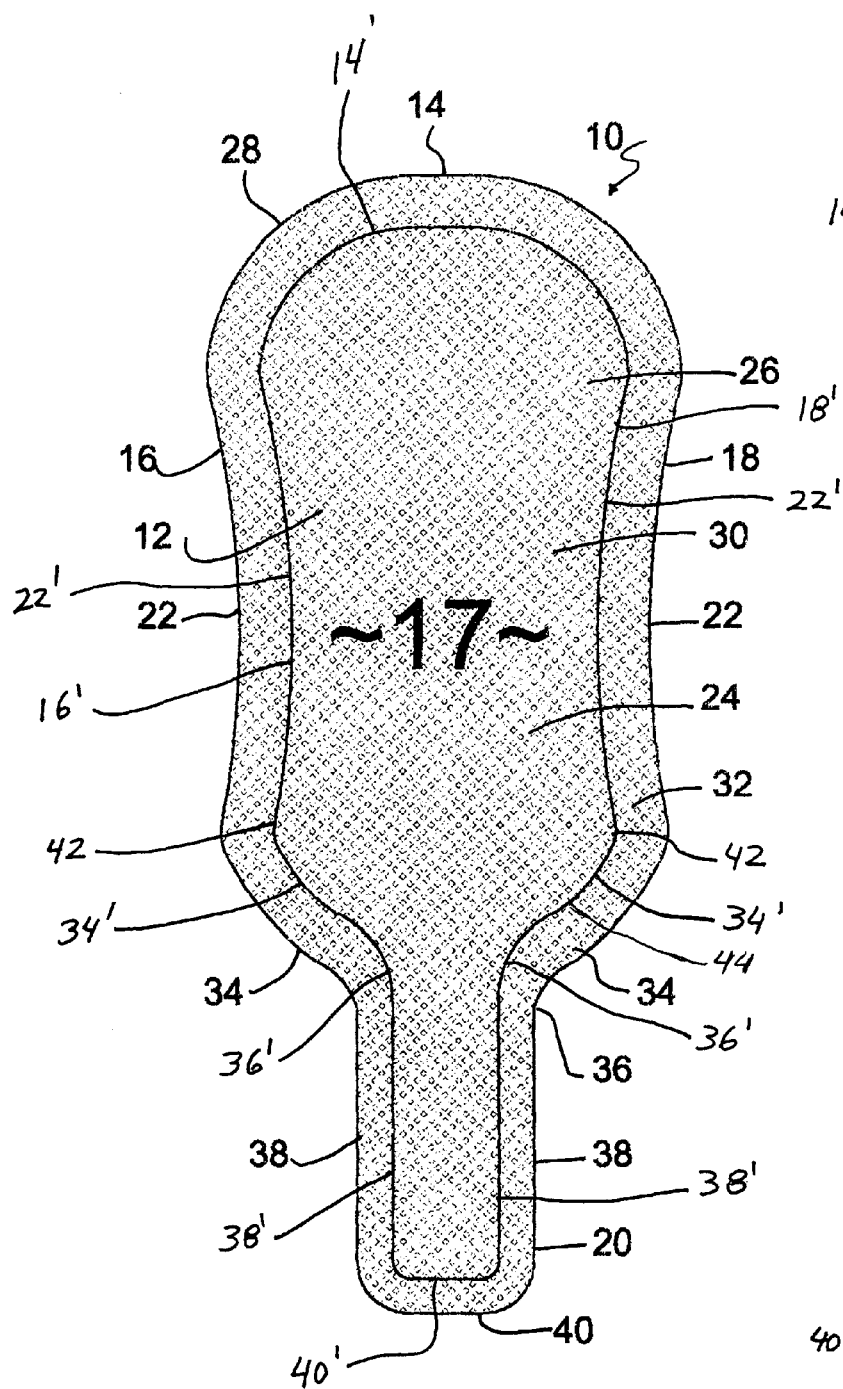
FIG. 5 Is a rear elevational view thereof.
Figure 3:
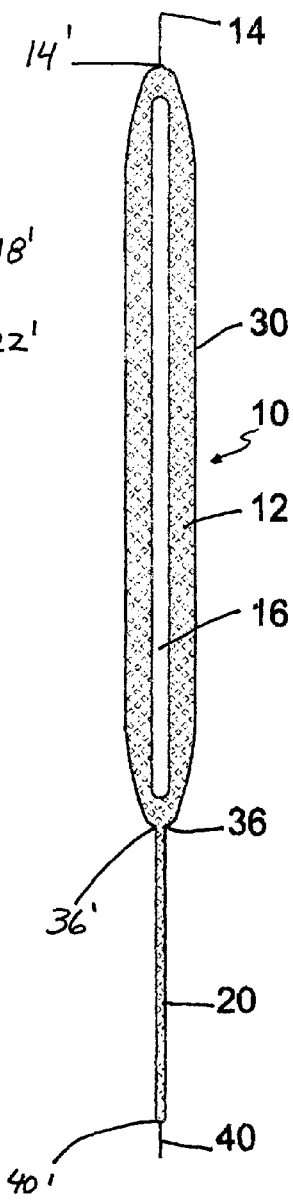
FIG. 3 Is a left side edge elevational view thereof.
Figure 4:
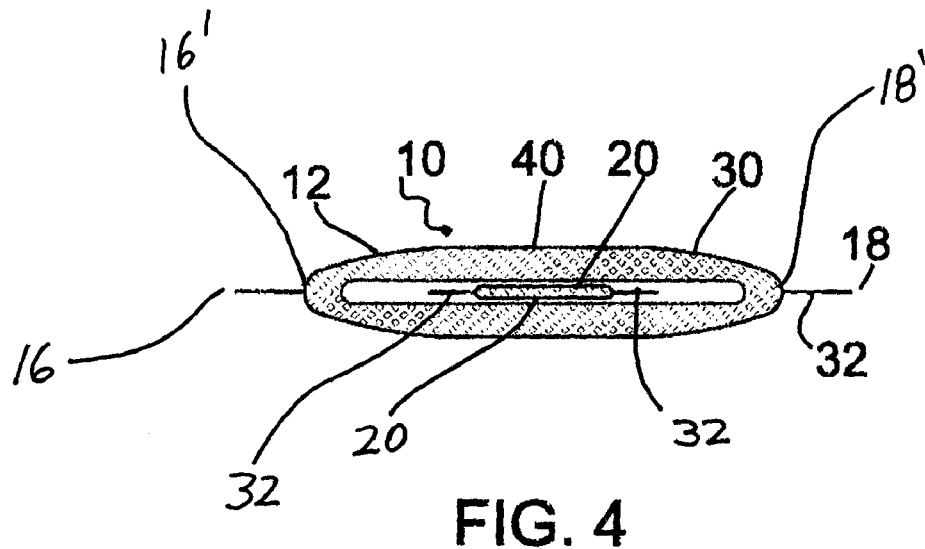
Figure 6:
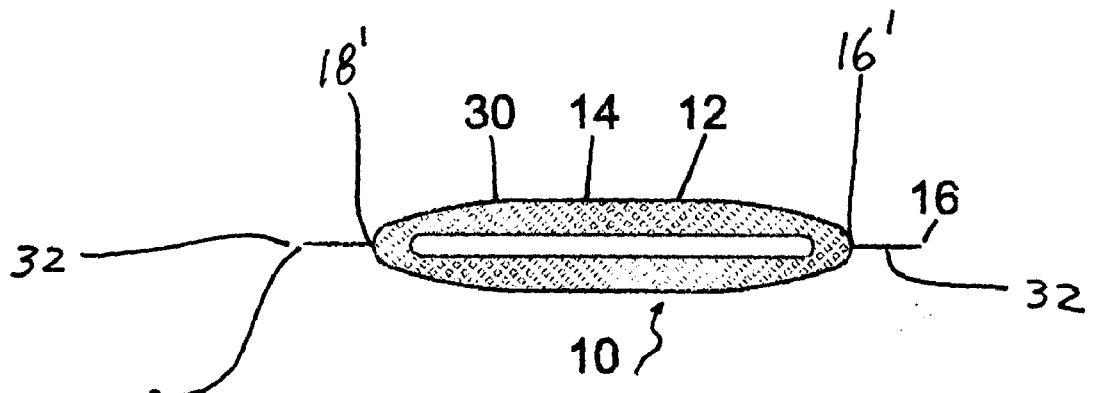

FIG. 1 is a top view of the feminine hygiene pad;
FIG. 2 is a right side view thereof;
FIG. 3 is a left side view thereof;
FIG. 4 is a rear end view thereof;
FIG. 5 is a bottom view thereof; and
FIG. 6 is a front end view thereof.

DETAILED DESCRIPTION OF THE PREFERRED EMBODIMENT

With reference to the drawings, FIG. 1 shows the feminine hygiene pad generally designated by the numeral 10. The feminine hygiene pad 10 has an absorbent front portion 12 having a longitudinal dimension between a front end 14 and a rear portion 20, and a transverse dimension between a left side edge 16 and a right side edge 18. The top view of the pad in FIG. 1 with top pad surface 15 is seen to be similar to the bottom view of the pad with bottom pad surface 17 in FIG. 3. The two side edges 16, 18 of the front portion are seen in FIG. 1 to have concave portions 22 which define a narrower mid-portion 24 in relation to the wider front 26 defined by convex front edge 28. The pad is also seen to have a thicker central portion or absorbent body 30 which is permanently bonded at its perimeter by bonded edge 32. The side edges 16,18 have convergent portions 34 which taper inwardly to a transition 36 from which extends the rear portion 20. The rear portion 20 is seen to have two straight mutually parallel sides 38 and a transverse rear edge 40. The side edges 38 are relatively long in relation to the rear edge 40 such that the rear portion is a generally rectangular elongated tab extending from the forward portion 12 along the longitudinal dimension. It will be further seen from the drawings that the rear portion 20 is much narrower than the front portion 12, and in the illustrated embodiment the width of the rear portion 20 is about one third the width between the side edges 16, 18 of the front portion 12. The drawings further show the rear portion to have a length, as measured along the side edges 22 from the transition 36 to the rear edge 40, also of about one third the length of the front portion as measured from the front end 14 to the transition 36. The elongated rear portion 20 is integral with the forward portion 12, and preferably is made of the same materials, the choice of which will be apparent to those skilled in the art.

As shown in the drawings, the forward pad portion 12 has a minimum transverse width which in the illustrated embodiment occurs at the narrowest point of the mid-portion 24 between the concavely shaped sides 22 of the forward portion 12. As shown, the rear portion 20 has a width between sides 38 which is less than half of this minimum transverse width. Stated otherwise, the absorbent forward pad portion 12 is at least twice the width of the rear portion at any point along the length of the forward pad portion, from front 14 to transition 36. The length of the forward pad portion from front 14 to transition 36 is substantially longer than the length of the rear portion measured between the transition 36 to rear 40, and as shown, the forward pad portion 12 is between one and one-half and twice the length of the rear portion 20.

The absorbent forward pad portion 12 is of sufficient length relative to the rear portion 20 to provide both an absorbent intermediate pad portion for receiving menstrual fluid and an absorbent front portion of the pad. The absorbent intermediate pad portion is generally the rear half of the forward pad portion 12, which as is well understood by users of such articles, tends to receive and collect the bulk of the menstrual fluid discharge. The absorbent front portion of the pad is generally the front half of the absorbent pad portion 12, and, as is also well understood by such users, provides extended coverage and containment of the fluid received and collected by the absorbent intermediate pad portion. From the foregoing, it may be understood that the pad 10 has three general portions, an absorbent front portion, an absorbent intermediate portion, and a rear portion.

As particularly appreciated in FIGS. 2, 3 and 4 of the drawings is that the entire pad 10 including absorbent forward portion 12 and rear portion 20 is substantially planar or essentially flat except for variations in pad thickness. That is, the rear portion 20 lies, at least in an initial condition of the hygienic pad, in a plane common to both the forward portion 12 and the rear portion 20 of the pad 10.

FIGS. 1 and 5 show the top pad surface 15 and bottom pad surface 17, respectively, to be continuous over both the absorbent forward portion 12 and the narrower tail portion 20.

In the particular embodiment depicted in FIGS. 2 and 3, the absorbent forward portion 12 of the pad is seen to be much thicker, due in part to the absorbent body 30, than the relatively thin rear portion 20 of the pad, as seen in the drawings.

The use and proper application of the hygiene pad 10 will be evident to those of the female gender by inspection of the drawings without further explanation. It may be briefly said that the wider forward portion is applied over the vaginal opening while the rearward appendage 20 is worn between and retained between the buttocks. This use of the rearward appendage 20 is evident from the widespread use among women of tong style undergarments which in part are similarly worn between the buttocks, in contrast to conventional briefs which are worn over the buttocks. The appendage 20 is thus able to retain the rear of the absorbent forward portion closer against the body following the contour of the crotch area and thereby better absorb and control rearward leakage of fluid from the vaginal area towards the rear of the thighs and the buttocks. This permits the user to sleep on her back with much reduced risk of rearward leakage of fluids. The elongated rear appendage is received between the user's buttocks and insures that the pad stays in place, and also replaces the wide rear end of conventional hygienic pads thereby reducing the size of the pad so that it can be more discreetly worn with small sized textiles and tight fitting garments.

An absorbent article; as apparent in FIGS. 1 through 6, the preferred embodiment consists of an absorbent body (1). The Absorbent body (1) is adhered or otherwise permanently bonded at its perimeter by the bonded edge. (2) A positioning point is formed on the main absorbent portion of the pad and an absorbent point is formed on the main portion of the pad. (3) The Elongated Rearward Appendage is fabricated of the same material as, and at the same time as the Absorbent body. The ELONGATED REARWARD APPENDICE is considered to be integral to the Absorbent Body (1) and the invention as a whole.

The following portion of the detailed description of the invention is made with reference to FIGS. 1 through 6 of the drawings in general and to particular Figures as may be indicated below.

As best seen in the top and bottom views of FIGS. 1 and 5 respectively, the rear portion 20 has a rear width between two side edges 38', the forward pad portion 12 has a front edge 14', two opposite forward side edges 16', 18' and a maximum forward width between the forward side edges. The forward side edges 16', 18' include convexly curved divergent side edge portions 34' for tapering the width of the forward pad portion to the rear width of the rear portion 20.

The rear portion has a maximum rear width between the rear side edges 38' of about one third of the maximum forward width. The rear portion 20 has a rear length from the rear edge 40' to the first transition 36' of the convexly curved divergent side edges 34' of about one third of a full pad length measured from the rear edge 40' to the front edge 14'. The pad 10 has a border 32 of relatively thin material which encompasses the pad along the side edges 16', 18', the rear edge 40' and the front edge 14'.

The divergent portions 34' of the forward side edges 16', 18' transition to non-divergent side edge portions 22' of the forward side edges at a second transition point 42 of the side edges 16', 18' such that the forward pad portion 12 measured along its longitudinal dimension from the second transition point 42 to the front edge 14' is substantially longer than the rear portion 20 measured from the rear edge 40' to the second transition point 42 along the longitudinal dimension.

The forward side edges 16', 18' each have an in-turned edge portion 22' located longitudinally between the divergent side edge portions 34' and the front edge 14' to define a narrower mid-portion 24 of the pad including a minimum width of the forward pad portion between the innermost points 25 of the in-turned edge portions 22'. Preferably the maximum width of the forward pad portion is located longitudinally between the narrower mid-portion 24 and the front edge 14', and the in-turned edge portions 22' are concavely curved.

The forward pad portion 12 increases in width between the divergent side edges 34' to a location 44 along its longitudinal dimension corresponding to a pad width of at least twice the rear width, and the forward pad portion 12 has a forward pad length measured from the aforesaid location 44 along its longitudinal dimension to a front edge 14' of the pad. The rear portion 20 has a rear length measured from the rear edge 40' along the longitudinal dimension to a point aligned with the same aforesaid location 44, the forward pad length being substantially longer than the rear length. As previously explained, a border 32 of relatively thin material encompasses the pad, such that the relative lengths of the forward pad length and the rear pad length are measured exclusive of the encompassing thin material 32 around the inner edges identified by primed numerals.

In a more general sense the invention concerns a feminine hygiene pad 10 having a wider absorbent forward pad portion 12, and a relatively narrow rear portion 20 adapted to be worn between the buttocks of a user. The rear portion 20 has a rear edge 40' and a rear width between rear side edges 38'. The forward pad portion 12 has forward side edges 16', 18' including divergent side edge portions 34' diverging from the rear side edges 38' and a second transition 42 from the divergent side edge portions 34' to non-divergent side edge portions 22'. The forward pad portion 12 has a mid-portion 24 of minimum width which is longitudinally located between the divergent side edge portions 34' and the front edge 14' of the pad, the minimum width being greater than the aforementioned rear width. More particularly, the said minimum width may be more than twice the rear width of the aforementioned rear portion 20.

In a presently preferred form, the pad 10 may be divided into three imaginary parts, one imaginary part comprising the rear portion 20, a second imaginary part comprising a one-half length of the forward pad portion 12 extending from the rear pad portion 20 to the aforementioned minimum width, and a third imaginary portion extending from the minimum width to the front edge 14', the three imaginary parts being of generally similar length along a longitudinal dimension of the pad between the rear edge 40' and the front edge 14'.

In the preferred form, the forward pad portion 12 is much wider than the rear pad portion 20 at all points along its length from the aforesaid second transition 42 to the front edge 14'.

The forward pad portion 12 tapers rearwardly in width between the divergent side portions 34' including a location 44 along the pad 10 at which the forward pad portion 12 is about twice the rear width, the pad 10 having a length between the location 44 and the front edge 14' which is substantially greater than a pad length between the said location 44 and the rear edge 40'.

The invention may also be understood as a feminine hygiene pad 10 having a wider absorbent forward pad portion 12 and a relatively narrow rear portion 20 adapted to be worn between the buttocks of a user, the rear portion 20 having a rear edge 40' and a rear width between rear side edges 38', the forward pad portion 12 having forward side edges 16', 18' including divergent side edge portions 34' diverging from the rear side edges 38' and a transition from the divergent side edge portions 34' to non-divergent side edge portions 22', the forward pad portion 12 being much wider than the rear pad portion 20 at all points along its length from the transition 42 to the front edge 14'. The forward pad portion 12 tapers in width between the divergent side portions 34' including at least one location 44 along the divergent sides 34' at which the width of the forward pad portion 12 is about twice the rear width, the pad 10 having a forward length between the aforesaid location 44 and the front edge 14' which is substantially greater than a rear pad length measured between the said location 44 and the rear edge 40'.

In all of the forms and embodiments of the invention described above, the pad lengths, measurements and proportions of the various pad portions are measured from inner pad edges identified by primed numerals as opposed to outer edges identified by similar but non-primed numerals, and are exclusive of the encompassing border portions 32 of thin material which defines the outer edges, such that border portions 32 are not included in those lengths, measurements and proportions. Likewise, all references to lengths, relative proportions and edges in the claims are understood to refer to the aforementioned inner edges, without regard to the thin sheet material encompassing the forward pad portion and the rear pad portion.

What is claimed is:

1. A feminine hygiene pad having a wider absorbent forward pad portion and a relatively narrow rear portion adapted to be worn between the buttocks of a user, said rear portion having a rear edge and a rare width between rear side edges, said forward pad portion having forward side edges including divergent side edge portions diverging from said rear side edges and a transition from said divergent side edge portions to non-divergent side edge portions, said forward pad portion increasing in width between said divergent side edges to a location along said longitudinal dimension corresponding to a pad width of at least twice said rear width;

said forward pad portion having a forward pad length measured from said location along said longitudinal dimension to a front edge of said pad;

said rear portion having a rear length measured from said rear edge to said location along said longitudinal dimension;

said forward pad length being at least one and one half times longer than said rear length; and a border of relatively thin material along at least some of said side edges, said rear edge and said front edge.

2. The feminine hygiene pad of claim 1 wherein said rear portion is integral with said forward pad portion.

3. The feminine hygiene pad of claim 1 wherein said rear portion is sized and shaped to be retained between the buttocks of a user of said pad.

4. The feminine hygiene pad of claim 1 wherein said absorbent forward pad portion is substantially thicker than a thickness of said rear portion.

5. The feminine hygiene pad of claim 1 wherein said absorbent forward pad portion is much thicker than a thickness of said rear portion.

6. The feminine hygiene pad of claim 1 wherein said forward pad portion has a wider front and a narrower mid-portion, said mid-portion being at least twice as wide as a width of said rear portion.

7. The feminine hygiene pad of claim 1 wherein said rear portion is made of the same material as the forward pad portion.

8. The feminine hygiene pad of claim 1 wherein said forward pad portion has an absorbent body bonded along a perimeter thereof by a bonded edge of said relatively thin material.

9. The feminine hygiene pad of claim 1, said hygiene pad further having a continuous upper surface and a continuous bottom surface, each said surface being common to said forward pad portion and said rear pad portion.

10. The feminine hygiene pad of claim 1 wherein said forward pad length is about twice as long as said rear length.

11. A feminine hygiene pad having a wider absorbent forward pad portion and a relatively narrow rear portion adapted to be worn between the buttocks of a user, said rear portion having a rear edge and a rear width between rear side edges, said forward pad portion having forward side edges including divergent side edge portions diverging from said rear side edges and a transition from said divergent side edge portions to non-divergent divergent side edge portions;

said forward side edges of said forward pad portion having inturned side edge portions defining therebetween a pad mid-portion of minimum width longitudinally located between pad portions of greater width than said minimum width and also longitudinally located between said transition and a front edge of said pad, said minimum width being greater than said rear width; and a border of relatively thin material along at least some of said side edges, said rear edge and said front edge.

12. The pad of claim 11 wherein said minimum width is more than twice said rear width of said rear portion.

13. The pad of claim 11 wherein said inturned side edges comprise concavely curved portions of said forward side edges.

14. The pad of claim 11 wherein said pad mid-portion of minimum width is located approximately midway between said divergent side edge portions and said front edge of said pad.

15. The pad of claim 11 wherein said forward pad portion increases in width between said divergent side edges to a location along said longitudinal dimension corresponding to a pad width of at: least twice said rear width;

said forward pad portion having a forward pad length measured from said location along said longitudinal dimension to a front edge of said pad;

said rear portion having a rear length measured from said rear edge to said location along said longitudinal dimension;

said forward pad length being substantially longer than said rear length.

* * * * *